US006629943B1

(12) United States Patent
Schroder

(10) Patent No.: US 6,629,943 B1
(45) Date of Patent: Oct. 7, 2003

(54) BUNION CORRECTION DEVICE

(76) Inventor: Mitchell J. Schroder, 4977 E. 169th St., Noblesville, IN (US) 46060

( * ) Notice: Subject to any disclaimer, the term of this patent is extended or adjusted under 35 U.S.C. 154(b) by 0 days.

(21) Appl. No.: 10/238,356

(22) Filed: Sep. 10, 2002

(51) Int. Cl.$^7$ .................................................. A61F 5/00
(52) U.S. Cl. ........................................................ 602/30
(58) Field of Search ............................ 602/30, 31, 4, 602/5, 22, 128, 893–894

(56) References Cited

U.S. PATENT DOCUMENTS

| | | | | |
|---|---|---|---|---|
| 353,910 A | * | 12/1886 | Zacharie | 602/30 |
| 643,068 A | * | 2/1900 | Pond | 602/30 |
| 804,406 A | * | 11/1905 | Hungad | 2/21 |
| 892,412 A | * | 7/1908 | Farra | 602/30 |
| 1,055,810 A | * | 3/1913 | Scholl | 602/30 |
| 1,213,786 A | * | 1/1917 | Wilms | 602/30 |
| 1,665,030 A | | 4/1928 | Hartwig | |
| 1,746,865 A | * | 2/1930 | Page | 602/30 |
| 2,596,038 A | * | 5/1952 | Mayer | 602/30 |
| 2,923,292 A | * | 2/1960 | Dorr | |
| 2,958,324 A | | 11/1960 | Berkemann | |
| 3,063,446 A | * | 11/1962 | Levitt | 602/30 |
| 3,209,750 A | * | 10/1965 | Levitt | |
| 3,219,032 A | * | 11/1965 | Levitt | 602/30 |
| 4,583,303 A | | 4/1986 | Laiacona et al. | |
| 4,632,103 A | * | 12/1986 | Fabricant et al. | 602/30 |
| 4,637,381 A | * | 1/1987 | Jungmann | 602/30 |
| 4,729,369 A | | 3/1988 | Cook | |
| 4,856,505 A | | 8/1989 | Shaffer et al. | |
| 5,174,052 A | | 12/1992 | Schoenhaus et al. | |
| 5,282,782 A | * | 2/1994 | Kasahara | 602/30 |
| 5,665,060 A | * | 9/1997 | Fabricant | 602/30 |
| 5,928,173 A | * | 7/1999 | Unruh | 602/30 |

* cited by examiner

*Primary Examiner*—Nicholas D. Lucchesi
*Assistant Examiner*—Huong Q. Pham
(74) *Attorney, Agent, or Firm*—C. John Brannon; Bingham McHale LLP

(57) ABSTRACT

A bunion correction device for providing lateral and torsional forces to one or more misaligned joints of the afflicted and deformed toe of a bunion sufferer, including a first toe-encircling ring and a second toe-encircling ring, and an elongated flexible member connecting the first and second toe-encircling rings and extending substantially beyond the toe-encircling rings. The toe-encircling rings are adapted to engage the patient's toe while the elongated flexible member is adapted to encirclingly engage the bunion patient's ankle. The elongated flexible member urges the toe-encircling rings to apply both a longitudinal and a torsional force component to the toe. The longitudinal and torsional force components then urge the misaligned joints of the bunion patient's toe into realignment.

11 Claims, 9 Drawing Sheets

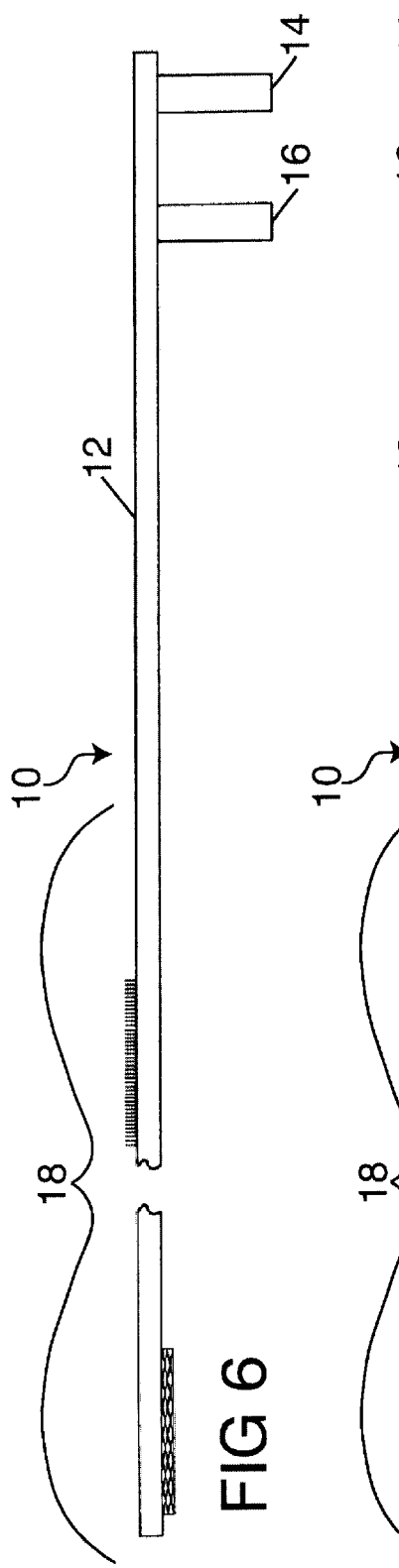
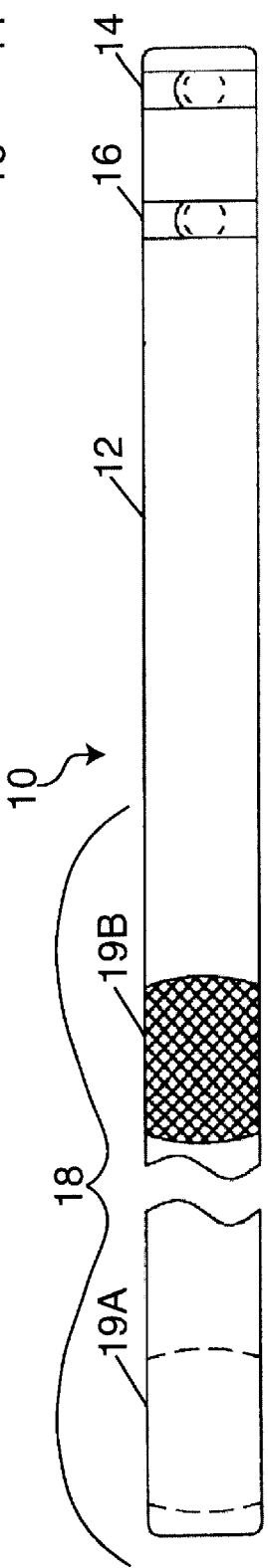
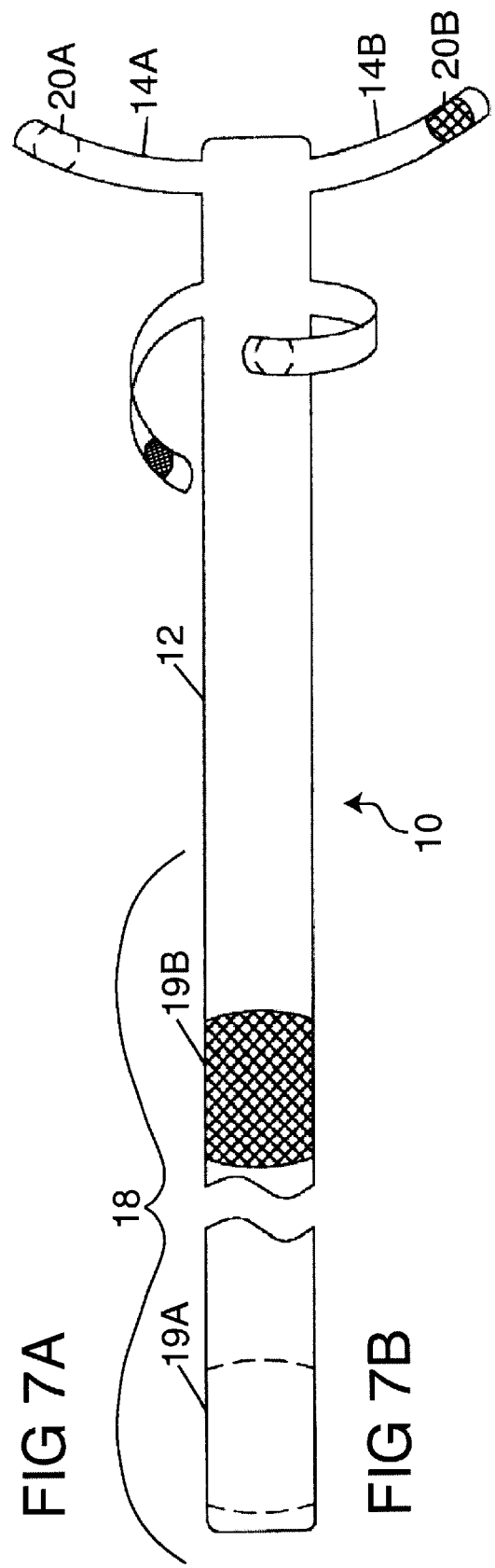
FIG 6
FIG 7A
FIG 7B

BUNION CORRECTION DEVICE

BACKGROUND OF THE INVENTION

A bunion, or hallux valgus, is the tilting of the toe away from the mid-line of the foot. FIG. 1 illustrates a bunion 5 as formed on one of a pair of feet. While bunions 5 can theoretically occur in any toe, they typically occur in the big toe 7 and only very occasionally in the little toe. Hallux valgus (although strictly referring to the big toe 7, the term 'hallux valgus' is used herein to generally refer to the bunion condition) is typically characterized by a lump or bump that is red, swollen and/or painful on the inside of the foot in and around the affected toe joint 9. 'Hallux valgus' literally describes what happens to the big toe 7. Hallux is the medical term for "big toe", and valgus is an anatomic term that means the deformity goes in a direction away from the midline of the body. So, in hallux valgus, the big toe 7 begins to point towards the outside of the foot (i.e., towards and usually over- or underlapping the other toes). As this condition grows worse, other changes occur in the foot that compound the problem. As illustrated in FIGS. 2–5, the bone just above the big toe 7 (the first metatarsal) usually develops too much of an angle in the other direction. This condition is called metatarsus primus varus. Metatarsus primus means "first metatarsal", and varus means that the deformity goes in a direction towards the midline of the body.

The joint 9 at the base of the big toe 7 is the most complex joint in the foot, comprising a pair of irregularly shaped bone or joint faces coming together to form a heavy load-bearing joint 9. Here the bones, tendons and ligaments work together to transmit and distribute the body's weight, especially during movement. Should this joint 9 become abnormally stressed over an extended period of time, a bunion 5 deformity may result. A bunion 5 is the protuberance of bone and/or tissue around the joint 9. The tissue enlargement occurs either at the base of the big toe 7 (a traditional bunion 5) or on the outside of the foot, at the base of the little toe (commonly referred to as a "bunionette" or "tailor's bunion").

Bunions 5 at the base of the big toe 7 usually begin when the big toe 7 starts moving toward the smaller toes, such as when tight, pointed shoes are worn. This crowding puts pressure on the joint 9, pushing it outward. The portions of the bones intersecting at and comprising the joint 9 therefore become hyper-rotated, resulting in the joint 9 moving outwardly as a result of the stresses upon it. The movement of the joint 9 in this outward direction initiates the formation of a bunion 5 as the joined bones are no longer collinear.

A common deformity of the big toe joint 9, a bunion 5 almost always mostly among people who wear shoes. Women are more frequently affected with bunions 5 because of their preference for tight, pointed, confining or high-heeled shoes. Wearing high heels is especially stressful on the joints of the foot because all of the body's weight rests there. The foot is then forced into a narrow, pointed "toe box", compounding the problem. Older people are also vulnerable to bunions 5 because of the higher incidence of arthritis affecting the big toe joint 9.

Bunions 5 are primarily a hereditary condition and, once begun, generally progressively worsen throughout life. However, it must be noted that it is the foot type that is hereditary, not the bunion 5 itself. People with flat feet or low arches are more prone to develop bunions 5 than those with higher arches. Bunions 5 also may be associated with various forms of arthritis. Arthritis can cause the joint's 9 protective covering of cartilage to deteriorate, leaving the joint 9 damaged and with a decreased range of motion.

As noted above, bunions 5 arise from mechanical instability within the foot, resulting in a misalignment of the bones therein and are typically characterized by the big toe 7 drifting either over or under the second toe. As a bunion 5 deformity progresses, a characteristic bump forms and grows behind the inside of the big toe 7. The act of walking requires the big toe 7 to support a great deal of the body's weight and therefore actuates the progression of the bunion 5. As the bunion 5 increases in severity, the condition may be complicated by the generation of other associated foot problems, such as hammertoes, painful calluses on the bottom of the foot, arch pain and the like.

Pain from a bunion 5 can range from mild to severe, making it difficult to walk in normal shoes, especially high-heeled shoes. The skin and deeper tissues around the bunion 5 may also become swollen or inflamed. Moreover, the other toes may be affected by the bunion 5, such as by result of pressure from the big toe 7 urging the lesser toes inwardly. Further, toenails may begin to grow into the sides of the nail bed. Likewise, the smaller toes can develop corns and/or become bent (hammertoes) and/or calluses may form on the bottom of the foot.

Bunion 5 treatments vary depending on the severity of pain and deformity related to the bunion 5. When left untreated, bunions 5 tend to grow larger and, usually, more painful. One common bunion treatment is to pad the bunion 5. While effective in diminishing the pain associated with the bunion 5, padding does not address the cause of the bunion 5. Likewise, switching from poorly fitting and constrictive shoes may lessen the pain from the bunion 5, but do not reverse the bunion condition.

Likewise, medications, such as anti-inflammatory drugs or cortisone injections may be administered to ease pain and inflammation caused by joint deformities. However, such medications do not correct or reverse such ongoing joint deformities. Physical therapy, such as through ultrasound treatment, whirlpool baths or other techniques can also provide temporary relief by easing the swelling and inflammation of the surrounding tissues.

There are a number of known devices for correcting bunions 5. One such device is described in U.S. Pat. No. 353,910, issued Dec. 7, 1886 to Zacharie and incorporated herein by reference. The '910 patent describes a leather-covered brass appliance that extends under the foot to connect the toe to the ankle. The '910 patent teaches application of a force upon the big toe 7 that pulls the big toe 7 away from the other toes but also back into the foot. Use of the '910 device therefore results in direct compression of the afflicted and enlarged joint 9.

U.S. Pat. No. 3,219,032, issued Nov. 23, 1965 to Levitt and incorporated herein by reference discloses a metallic bunion splint worn on the foot, engaging the big toe 7 and anchored around the heel. The '032 splint exerts a lateral transverse force on the big toe 7, pulling it out and away from the other toes. The '032 splint, however, does not directly address the cause of the bunion joint deformity (i.e., derotation of the joint), but instead only addresses the symptom (i.e., the misaligned toe).

Probably the most extreme treatment for bunions 5 is surgery. While pain and deformity are significantly reduced in the great majority of patients who undergo bunion surgery, bunion surgery in and its associated recovery can be both painful and costly. Moreover, the recovery period is relatively slow since the surgery involves manipulation and alteration of intricate load-bearing bones. Further, postoperative orthoses and/or supportive devices are often required to improve foot function.

Bunion surgical procedures range from removal of the enlarged portion of bone and the realignment of the muscles, tendons and ligaments surrounding the joint 9 through the cutting of the bone to facilitate a shift to its proper position (which may likewise involve moving the surrounding tendons and ligaments) to a combination of the removal of the enlarged portion of the bone; cutting and realignment of the bone; and correction of the tendons and ligaments. If the joint 9 is destroyed beyond repair (commonly seen in arthritis), it may need to be reconstructed or replaced with an artificial joint. Joint replacement implants may be used in the reconstruction of the big toe joint 9.

There exist a number of wearable devices and appliances designed to correct bunion. conditions without surgery. These tend to involve splints or like devices that pull the afflicted toe 7 away from the other toes back towards its orientation parallel to the mid-line of the foot. While useful, the known devices tend to be bulky and uncomfortable. Moreover, the known devices have not substantially eliminated the need for bunion surgery.

There therefore remains a need for a bunion correction device that is more effective in correcting bunion conditions by addressing the cause of the bunion 5 instead of merely the symptom, thereby reducing and/or eliminating the requirement for bunion corrective surgery. The present invention addresses this need.

SUMMARY OF THE INVENTION

The present invention relates to a method and apparatus for the non-surgical correction of bunion conditions. One object of the present invention is to provide an improved bunion correction appliance. Related objects and advantages of the present invention will be apparent from the following description.

BRIEF DESCRIPTION OF THE DRAWINGS

FIG. 6 is a side-elevational schematic view of a first embodiment of the present invention.

FIG. 7A is a top plan view of the embodiment of FIG. 6 with closed toe-engaging rings.

FIG. 7B is a top plan view of FIG. 7A but with open toe-engaging rings.

DESCRIPTION OF THE PREFERRED EMBODIMENTS

Figure 1:
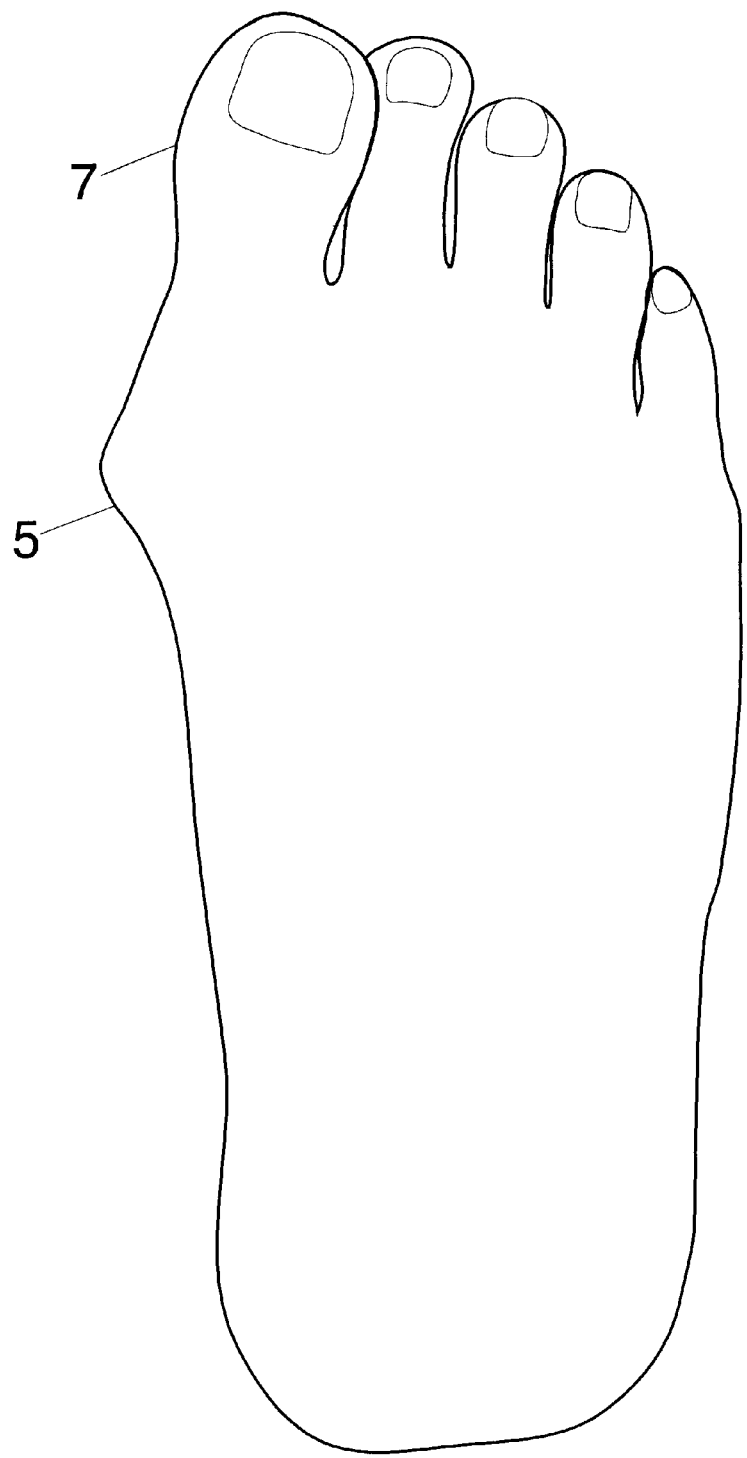
FIG. 1 is a top plan schematic view of a foot having a bunion condition of the big toe.
Figure 2:
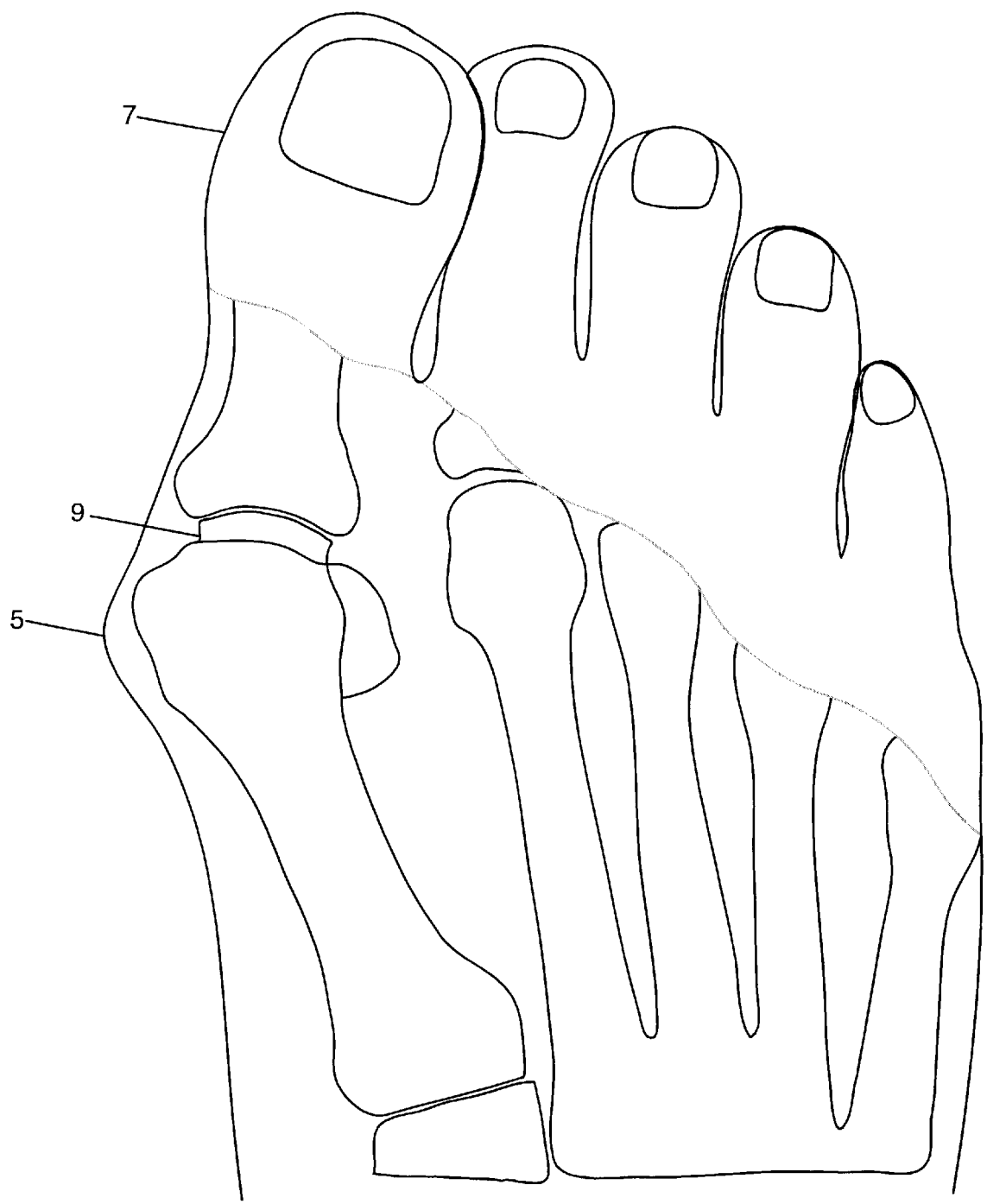
FIG. 2 is an enlarged partial cut-away view of FIG. 1.
Figure 3:
FIG. 3 is a partial cut-away schematic view of a pair of feet, one having a bunion condition.
Figure 4:
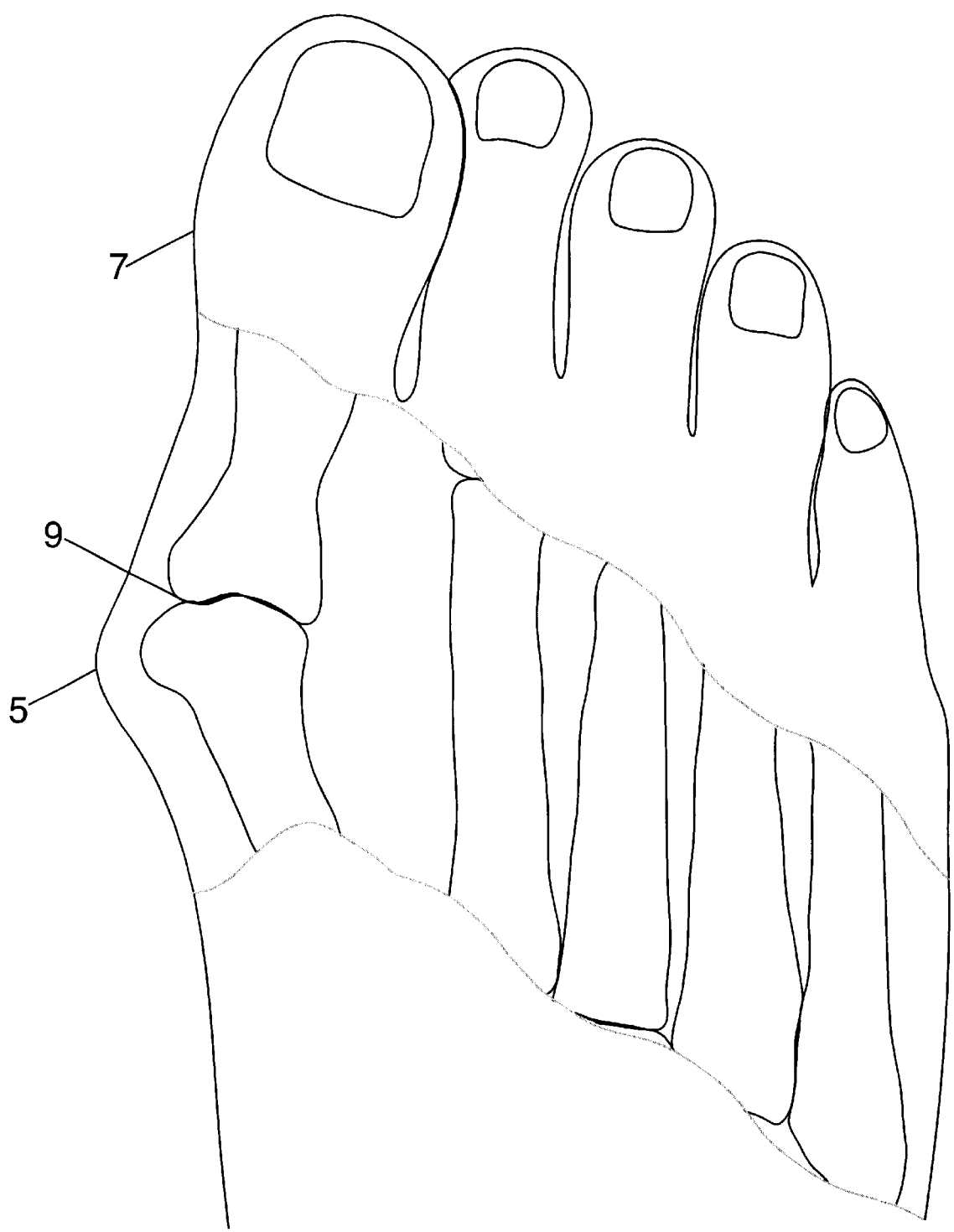
FIG. 4 is an enlarged partial cut-away view of the bunion-afflicted foot of FIG. 3.
Figure 5:
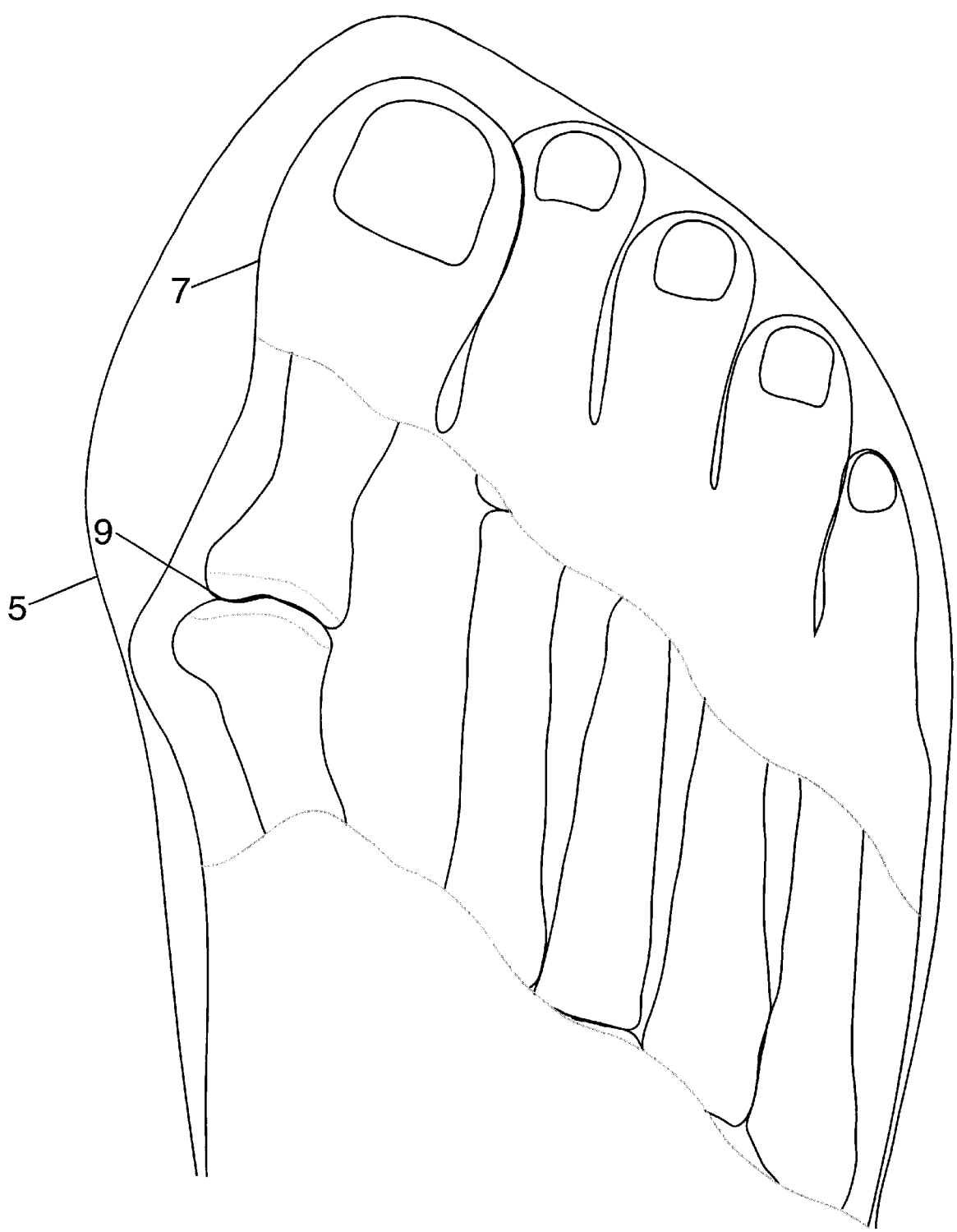
FIG. 5 is a view of the foot of FIG. 4 including the boundary of a shoe worn thereupon.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 8:
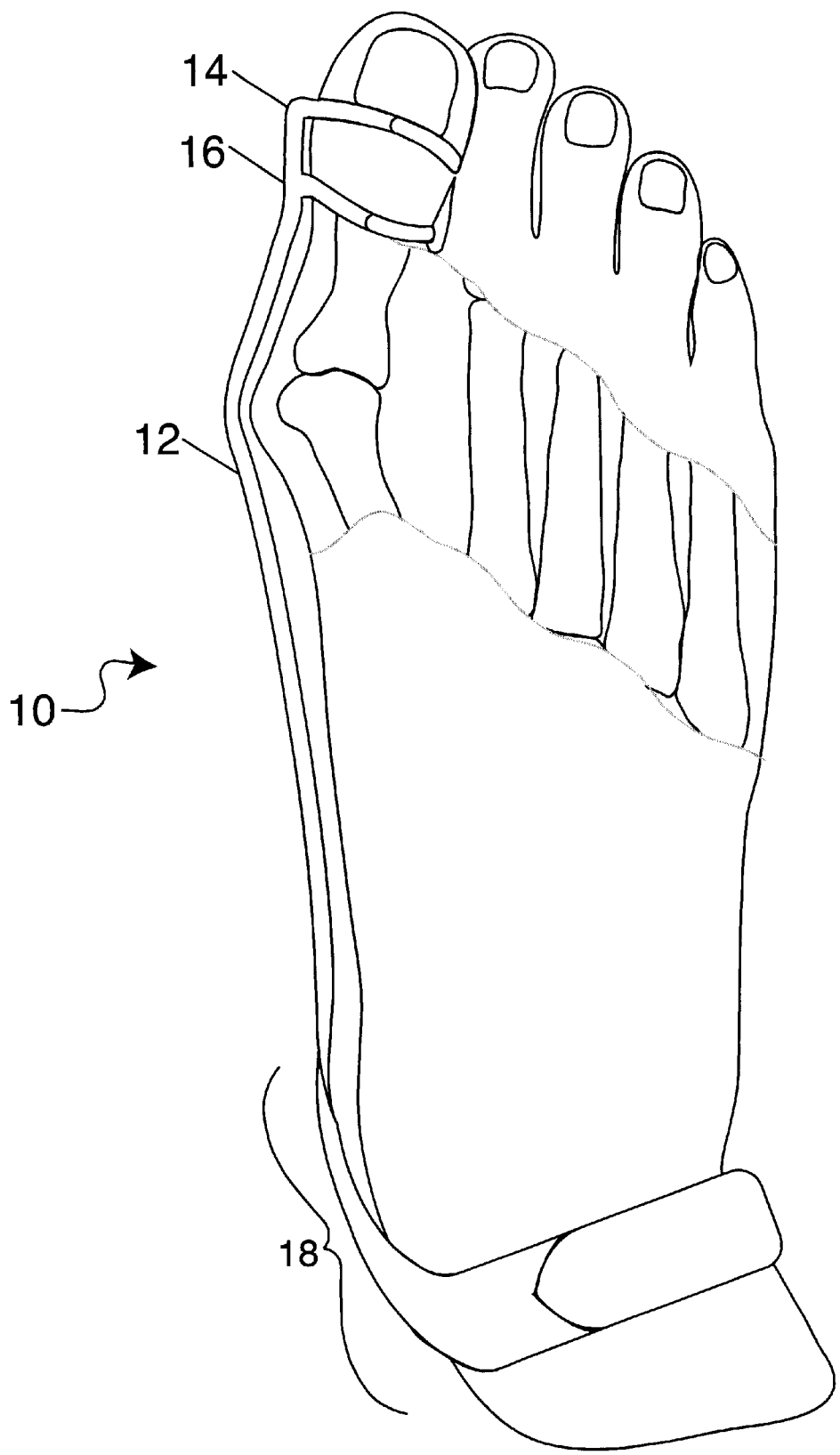
FIG. 8 is a top plan schematic view of the embodiment of FIG. 6 engaging a bunion afflicted foot.

A first embodiment of the present invention is illustrated in FIGS. 6–8. The invention comprises a bunion correction appliance 10 including a flexible elongated member 12 extending between a first and second toe-engaging ring 14, 16 and an ankle-engaging portion 18. The flexible elongated member 12 is preferably formed of a stiff, semi-rigid material, such as a polymer-based material (i.e., nylon), leather or the like, although the flexible elongated material may alternately be formed from a material having elastic properties (such as rubber). The flexible elongated member preferably has dimensions of about 18 inches long and about ½ inch in diameter, although the elongated member may be formed to any convenient length and width to accommodate a patient's foot size.

The ankle-engaging portion 18 further includes a first and second interlocking fastener portion 19A and B. Preferably, the interlocking fastener portions 19A and B are of the hook-and-loop type, but interlocking fastener portions 19A and B may alternately be of any convenient type, such as a buckle assembly (tongue and clasp), tab and slot, male-into-female snap assembly, or the like. In the preferred embodiment, the ankle-engaging portion 18 is adapted to be looped about the ankle and secured to itself, such that the appliance 10 is secured or anchored at one end to the ankle.

The toe-engaging rings 14, 16 are preferably adjustable in size, but may alternately be formed as solid, non-adjustable rings (such as steel rings). More preferably, the toe-engaging rings 14, 16 are formed as partial rings (14A and B and 16A and B) extending from the elongated member 12, with a ring locking assembly 20 attached thereto. The toe-engaging rings 14, 16 may be made out of any convenient material, but are preferably formed of the same material as the elongated member 12. Preferably, each partial ring portion 14A, 14B, 16A, 16B, has an interlocking portion (20A, 20B) of ring locking assembly 20 attached thereto. Preferably, the interlocking portions 20A and B are hook-and-loop type connectors, although any convenient connector means may be selected.

In operation, a bunion sufferer dons the appliance 10 by coupling the toe-engaging rings 14, 16 the toe of the foot afflicted with the bunion 5 (for the purposes of illustration, it is assumed that the afflicted toe is the big toe 7). Preferably, the last joint of the big toe 7 is positioned between the toe-engaging rings 14, 16 such that the last joint (i.e., the fifth MP joint), while not the afflicted joint 9, will likewise by subjected to corrective forces as the appliance 10 is worn. Next, the appliance 10 is extended adjacent the foot, over or adjacent the bunion 5, and to the ankle, where the ankle-engaging portion 18 is coupled to the ankle. This is preferably done by wrapping the ankle-engaging portion 18 snugly about the ankle and engaging the interlocking fastener portions 19A and B. The appliance 10 should be pulled taught before the ankle-engaging portion 18 is coupled to the ankle, such that the appliance exerts a corrective force onto the big toe 7 urging the big toe 7 back into its properly aligned position. Preferably, the appliance exerts a force onto the big toe 7 having a substantial torsional component and a substantial linear component. The linear component urges the big toe 7 linearly outwardly away from the other toes, while the torsional component derotates the big toe 7 to urge the joint 9 faces back together. In other words, the appliance exerts a force onto the big toe 7 that both pulls it away from the foot and twists the joint 9 back together.

Figure 9:
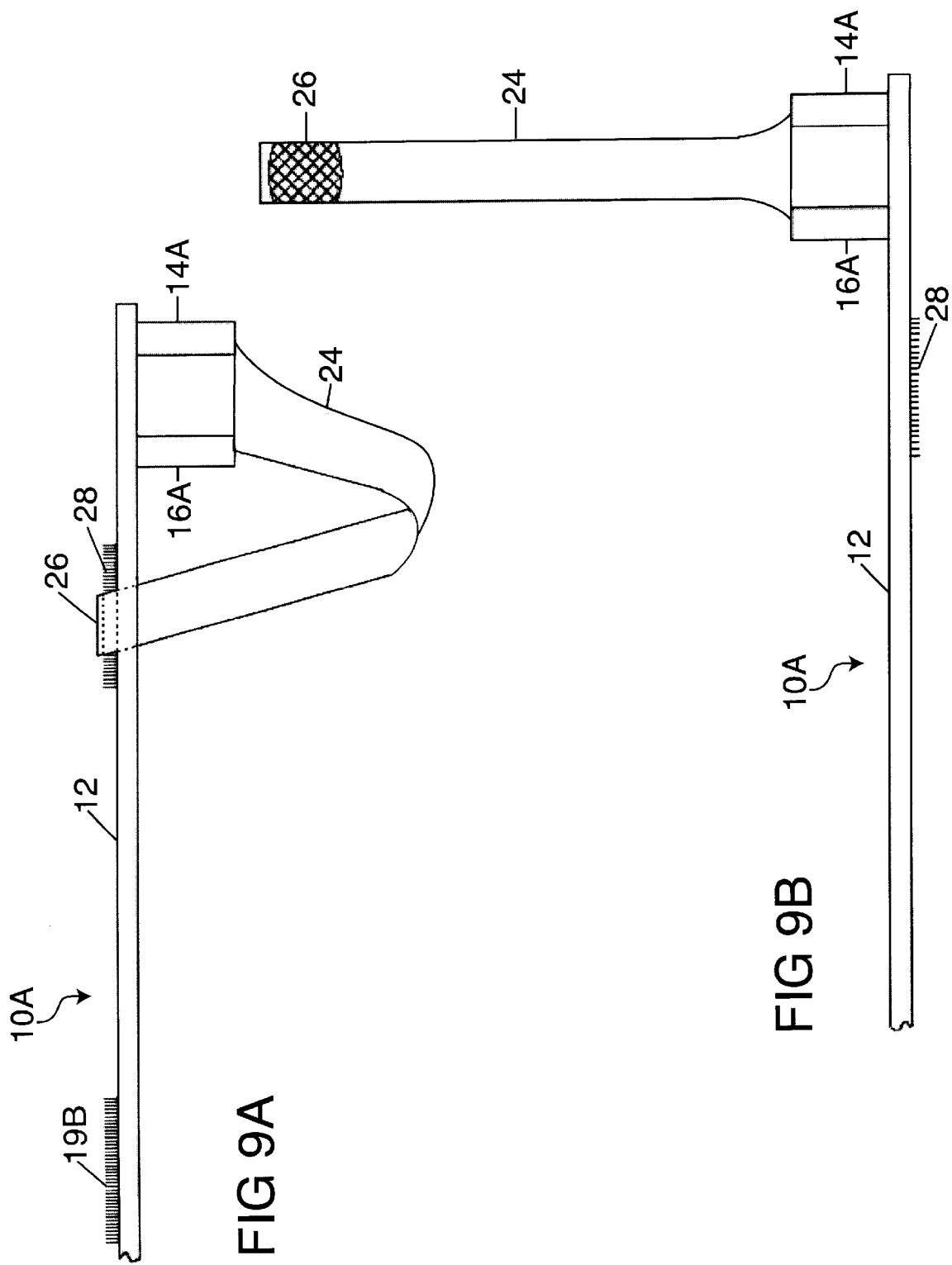
FIG. 9A is a partial side elevational view of a second embodiment of the present invention.
FIG. 9B is a partial side elevational view of the embodiment of FIG. 9B with the torsion strap extended.
Figure 10:
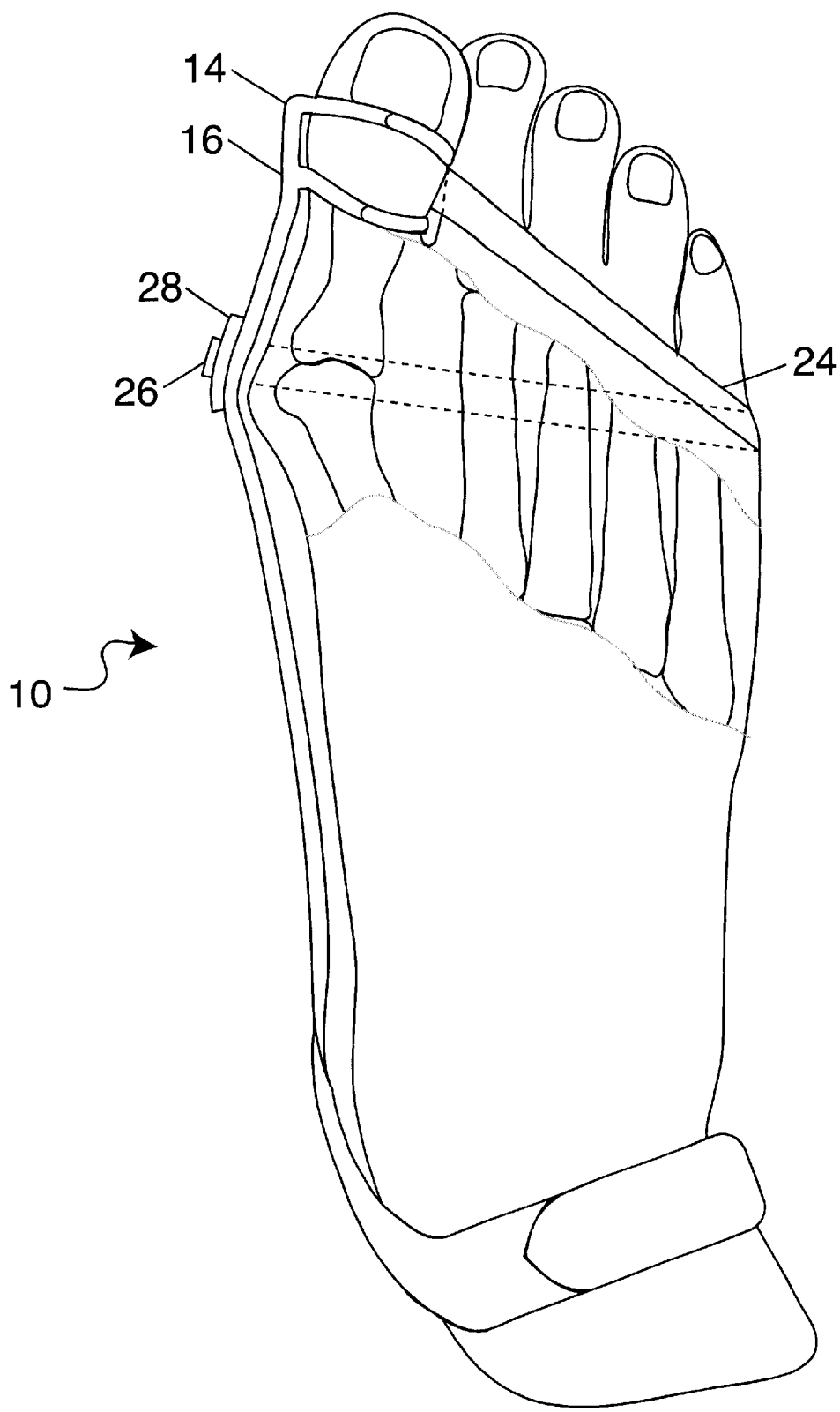
FIG. 10 is a top plan schematic view of the embodiment of FIG. 9A engaging a bunion afflicted foot.

FIGS. 9A–10 illustrate a second embodiment of the present invention, and appliance 10A identical to the appliance 10 described above, but with the addition of a transverse band 24 that extends from a fixed connected position on the elongated portion 12A and includes a first connector portion 26 affixed thereto near the free end. The transverse band 24 preferably extends from the elongated member 12A from between the toe-engaging rings 14A and 16A. The elongated connector has a second, mating connector portion 28 affixed thereto, preferably positioned near the second toe-engaging ring 16A. The transverse member 24 is preferably formed of an elastic material, such as rubber, but may alternately be formed of a substantially inelastic flexible material, such as nylon.

In use, the transverse portion is engaged after the appliance 10A is connected (as described above) by guiding the transverse member 24 over and around the foot. The transverse member 24 is pulled taught and the connector portions 26, 28 are lockingly engaged. The transverse member 24 exerts a torque onto the big toe 7, to further urge derotation of the big toe 7. While the transverse member 24 also contributes a longitudinal force on the big toe 7 opposite the longitudinal force contributed by the elongated member 12, the magnitudes of the two force contributions are such that the net longitudinal force on the big toe 7 is sufficient to urge the big toe 7 away from the other toes. In other words, the magnitude of the longitudinal force contribution from the elongated member 12 is substantially greater than the magnitude of the longitudinal force contribution from the transverse member 24. Preferably, the torque contribution from the transverse member 24 is sufficient to urge derotation of the big toe 7 such that the big toe 7 is simultaneously longitudinally pulled away from the remaining toes and derotated back into the desired orientation.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A bunion correction device for providing lateral and torsional forces to the misaligned joints of a bunion patient's toe, comprising:
    a first toe-encircling ring structure to engage one side of a toe, joint;
    a second toe-encircling ring structure to engage an opposite side of the toe joint;
    a first elongated flexible member connecting the first and second toe-encircling rings and extending substantially beyond the toe-encircling rings; and
    a second elongated member connected to at least one toe-encircling ring and connectable to the first elongated member;
    wherein the first elongated flexible member is adapted to encirclingly engage the bunion patient's ankle;
    wherein the second elongated member is adapted to encirclingly engage the patient's foot in an orientation generally perpendicular to the first elongated member;
    wherein the first elongated flexible member urges the toe-encircling rings to apply both a substantial longitudinal and a substantial torsional force component to the toe; and
    wherein the substantial longitudinal and torsional force components urge the misaligned joints of the bunion patient's toe into realignment.

2. The device of claim 1 wherein each toe-encircling ring is independently adjustable to snugly engage the toe.

3. An appliance for use by a patient to correct a bunion condition involving misaligned toe joints, comprising:
    a pair of toe rings, each having an adjustable diameter;
    a substantially inelastic semi-rigid connecting member connecting the pair of toe rings;
    an elongated substantially inelastic semi-rigid ankle-engaging member extending from the connecting member;
    wherein the ankle-engaging member is adapted to snugly engage the patient;
    wherein the pair of toe rings is adapted to actuate a first force having a first non-zero linear and a first non-zero torsional component on a joint positioned therebetween to urge the joint into alignment;
    wherein the ankle-engaging member is adapted to actuate a second force having a second non-zero linear and a second non-zero torsional component on at least one misaligned toe joint.

4. The appliance of claim 3 wherein each toe ring further comprises a respective hook-and-loop fastener operationally coupled thereto to actuate adjustment of the diameter.

5. The appliance of claim 3 wherein the ankle engaging member further comprises an ankle-engaging hook-and-loop fastener operationally connected thereto to actuate engagement of the ankle.

6. The appliance of claim 3 wherein the pair of toe rings comprises a first and a second toe ring and wherein the first and second toe rings are positioned on either side of a patient's fifth MP joint.

7. The appliance of claim 3 wherein the ankle-engaging member extends from the toe to the ankle, wherein the ankle-engaging member engages the bunion, and wherein the bunion operates as a filcrum to facilitate direction of the second force.

8. A method for aligning misaligned toe joints to correct a bunion condition in a patient having a toe afflicted by a bunion, comprising the steps of:
    a) positioning a pair of toe-engaging members on opposite sides of a toe joint;
    b) connecting the toe-engaging members to the patient's leg via an elongated member;
    c) substantially eliminating slack in the elongated member to exert a biasing force on the toe through the toe-engaging members; and
    d) positioning the elongated member in pivotal contact with the bunion and engaging the elongated members to the patient's anklet
    wherein the biasing force has a first linear and a first torsional component acting between the toe-engaging members; and
    wherein the biasing force has a second linear and a second torsional component acting on a toe joint outside of the space between pair of toe-engaging members.

9. The method of claim 8 wherein the first and second linear forces urge the engaged toe away from neighboring toes and wherein the second torsional force urges rotation of the toe joint into alignment.

10. A method for aligning misaligned bunion joints in a patient having a toe afflicted by a bunion and misaligned towards neighboring toes, comprising the steps of:

a) positioning a first toe-engaging member on a first side of a toe joint spaced from the bunion;
b) positioning a second toe-engaging member opposite the first toe-engaging member and on a second side of the toe joint;
c) connecting the first and second toe-engaging members with an elongated member;
d) connecting the elongated member to the patient's ankle;
e) tightening the elongated member to urge the toe away from the neighboring toes, wherein the toe is urged transversely away from the neighboring toes; and
wherein the bunion joint is rotationally urged into alignment.

11. A method for realigning misaligned joints in a foot of a bunion patient, comprising the steps of:
a) positioning a first toe-engaging ring on a first side of a misaligned toe joint;
b) positioning a second toe-engaging ring on a second side of the toe joint and opposite the first toe-engaging ring;
c) connecting an elongated member to the first and second toe-engaging rings; and to the patient's ankle;
d) exerting a first nonzero transverse biasing force on the toe urging the toe away from a neighboring toe; and
e) exerting a first nonzero rotational force on the misaligned joint rotationally urging the misaligned joint towards realignment;
f) connecting an elongated transversely biasing member to the first and second toe-engaging rings and to the elongated member; and
g) exerting a second nonzero transverse biasing force on the toe urging the toe away from a neighboring toe.

* * * * *

UNITED STATES PATENT AND TRADEMARK OFFICE
CERTIFICATE OF CORRECTION

PATENT NO.    : 6,629,943 B1
DATED         : October 7, 2003
INVENTOR(S)   : Mitchell J. Schroder It is certified that error appears in the above-identified patent and that said Letters Patent is hereby corrected as shown below:

<u>Column 6,</u>
Line 39, the word "filcrum" should be replaced with -- fulcrum. --

Signed and Sealed this

Ninth Day of December, 2003

JAMES E. ROGAN
*Director of the United States Patent and Trademark Office*